United States Patent
Greenhalgh et al.

(10) Patent No.: US 10,842,513 B2
(45) Date of Patent: Nov. 24, 2020

(54) METHODS FOR ADVANCING INVERTING MECHANICAL THROMBECTOMY APPARATUSES IN THE VASCULATURE

(71) Applicant: STRYKER CORPORATION, Fremont, CA (US)

(72) Inventors: E. Skott Greenhalgh, Gladwyne, PA (US); Michael P. Wallace, Pleasanton, CA (US)

(73) Assignee: Stryker Corporation, Fremont, CA (US)

(*) Notice: Subject to any disclaimer, the term of this patent is extended or adjusted under 35 U.S.C. 154(b) by 155 days.

(21) Appl. No.: 15/794,939

(22) Filed: Oct. 26, 2017

(65) Prior Publication Data
US 2018/0042624 A1     Feb. 15, 2018

Related U.S. Application Data

(62) Division of application No. 15/496,786, filed on Apr. 25, 2017, now Pat. No. 10,010,335.
(Continued)

(51) Int. Cl.
*A61B 17/22* (2006.01)
*A61B 17/221* (2006.01)
(Continued)

(52) U.S. Cl.
CPC ............ *A61B 17/22* (2013.01); *A61B 17/221* (2013.01); *A61B 17/22031* (2013.01);
(Continued)

(58) Field of Classification Search
CPC .......... A61B 17/22031; A61B 17/3417; A61B 2017/22034; A61B 2017/22035;
(Continued)

(56) References Cited

U.S. PATENT DOCUMENTS

| 4,222,380 A | 9/1980 | Terayama |
| 4,243,040 A | 1/1981 | Beecher |

(Continued)

FOREIGN PATENT DOCUMENTS

| AU | 2015210338 | 8/2015 |
| GB | 1588072 | 4/1981 |

(Continued)

OTHER PUBLICATIONS

Invitation to Pay Additional Fees for International Patent Appln. No. PCT/US2018/059607 dated Jan. 31, 2019.
(Continued)

*Primary Examiner* — Wade Miles
*Assistant Examiner* — Kankindi Rwego
(74) *Attorney, Agent, or Firm* — Vista IP Law Group, LLP

(57) ABSTRACT

Mechanical thrombectomy apparatuses (devices, systems, etc.) and methods for positioning them within a vessel and using them to remove a thrombus, e.g., clot, from within a vessel. In particular, described herein are methods of advancing an inverting tractor thrombectomy apparatus having a tractor comprising a flexible tube of material that inverts over itself as it rolls over a distal end opening of an elongate inversion support by extending the tractor region and/or a puller coupled to the tractor distally beyond the end of the catheter. Also described herein are power-driven mechanical thrombectomy apparatuses.

10 Claims, 13 Drawing Sheets

Related U.S. Application Data

(60) Provisional application No. 62/327,024, filed on Apr. 25, 2016.

(51) Int. Cl.
    *A61B 17/00* (2006.01)
    *A61B 17/34* (2006.01)

(52) U.S. Cl.
    CPC .............. *A61B 2017/00398* (2013.01); *A61B 2017/2215* (2013.01); *A61B 2017/22038* (2013.01); *A61B 2017/22075* (2013.01); *A61B 2017/22079* (2013.01); *A61B 2017/3435* (2013.01)

(58) Field of Classification Search
    CPC   A61B 2017/22038; A61B 2017/22041; A61B 2017/22045; A61B 2017/22075; A61B 2017/22079; A61B 2017/3435; A61B 17/22; A61B 17/221; A61B 2017/00398; A61B 2017/2215; A61M 25/003; A61M 25/0067; A61M 25/0068; A61M 25/0069; A61M 25/0074; A61M 25/0082; A61M 25/0113; A61M 25/0119; A61M 25/01; A61M 25/013; A61M 25/014; A61M 2025/0006; A61M 2025/0031; A61F 2/95; A61F 2/966
    USPC ....................................................... 606/114
    See application file for complete search history.

(56) References Cited

U.S. PATENT DOCUMENTS

| | | |
|---|---|---|
| 4,324,262 A | 4/1982 | Hall |
| 4,469,100 A | 9/1984 | Hardwick |
| 4,604,094 A | 8/1986 | Shook |
| 4,646,736 A | 3/1987 | Auth |
| 4,863,440 A | 9/1989 | Chin |
| 4,946,440 A | 8/1990 | Hall |
| 5,329,923 A | 7/1994 | Lundquist |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,156,055 A | 12/2000 | Ravenscroft |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Brook et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm |
| 9,186,487 B2 | 11/2015 | Dubrul et al. |
| 9,358,037 B2 | 1/2016 | Farhangnia et al. |
| 9,259,237 B2 | 2/2016 | Quick et al. |
| 9,351,747 B2 | 5/2016 | Kugler et al. |
| 9,463,035 B1 | 10/2016 | Greenhalgh et al. |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 1,001,033 A1 | 7/2018 | Greenhalgh et al. |
| 1,001,626 A1 | 7/2018 | Hauser |
| 1,002,875 A1 | 7/2018 | Wallace et al. |
| 1,013,038 A1 | 11/2018 | Farhangnia et al. |
| 1,027,186 A1 | 4/2019 | Greenhalgh et al. |
| 1,032,788 A1 | 6/2019 | Yachia |
| 2002/0032455 A1 | 3/2002 | Boock et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0176884 A1 | 9/2003 | Berrada et al. |
| 2003/0208224 A1 | 11/2003 | Broome |
| 2004/0098033 A1 | 5/2004 | Leeflang et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0283166 A1 | 12/2005 | Greenhalgh |
| 2005/0283186 A1 | 12/2005 | Berrada et al. |
| 2006/0042786 A1 | 3/2006 | West |
| 2006/0089533 A1 | 4/2006 | Ziegler et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0276874 A1 | 12/2006 | Wilson et al. |
| 2006/0293696 A1 | 12/2006 | Fahey et al. |
| 2007/0112374 A1 | 5/2007 | Paul, Jr. et al. |
| 2007/0149996 A1 | 6/2007 | Coughlin |
| 2007/0213765 A1 | 9/2007 | Adams et al. |
| 2008/0183136 A1 | 7/2008 | Lenker et al. |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desai et al. |
| 2010/0190156 A1 | 7/2010 | Van Wordragen et al. |
| 2010/0249815 A1 | 9/2010 | Jantzen et al. |
| 2011/0034987 A1 | 2/2011 | Kennedy |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1* | 11/2011 | Martin ................. A61B 17/221 606/159 |
| 2012/0083824 A1 | 4/2012 | Berrada et al. |
| 2012/0083868 A1 | 4/2012 | Shrivastava |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0046133 A1 | 2/2014 | Nakamura et al. |
| 2014/0155980 A1 | 6/2014 | Turjman |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0164523 A1 | 6/2015 | Brady et al. |
| 2015/0164666 A1 | 6/2015 | Johnson et al. |
| 2015/0190155 A1 | 7/2015 | Ulm, III |

(56) References Cited

U.S. PATENT DOCUMENTS

| | | |
|---|---|---|
| 2015/0190156 A1 | 7/2015 | Ulm, III |
| 2015/0196380 A1 | 7/2015 | Berrada et al. |
| 2016/0022293 A1 | 1/2016 | Dubrul et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0112513 A1 | 4/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0348014 A1 | 12/2017 | Wallace et al. |
| 2018/0042624 A1 | 2/2018 | Greenhalgh et al. |
| 2018/0042626 A1 | 2/2018 | Greenhalgh et al. |
| 2018/0070968 A1 | 3/2018 | Wallace et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0033614 A1 | 11/2019 | Greenhalgh et al. |

FOREIGN PATENT DOCUMENTS

| | | |
|---|---|---|
| GB | 2498349 | 7/2013 |
| WO | 00/32118 | 6/2000 |
| WO | WO 2009086482 | 7/2009 |
| WO | 2012/009675 | 1/2012 |
| WO | 2012/049652 | 4/2012 |
| WO | WO 2012162437 | 11/2012 |
| WO | 2017/058280 | 4/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appln. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/201502281 93218/http://www.edwards.com/products/vascular/atraumaticocclusion/pages/occlusioncatheter.aspx; ©2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
YOUTUBE; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
COVIDIEN; Solitaire(TM) As Neurovascular Remodeling Device (product information); retrieved from the internet: http://www.ev3.net/neuro/intl/remodeling-devices/solitaire-ab.htm; ©2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
Non-Final Office Action for U.S. Appl. No. 15/496,570, dated Aug. 9, 2017.

(56) References Cited

OTHER PUBLICATIONS

PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appn. No. 15/291,015.
Non Final Office Action dated Aug. 23, 2019 for U.S. Appl. No. 15/700,685.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Non Final Office Action dated Dec. 27, 2019 for U.S. Appl. No. 16/594,256.
Amendment Response dated Mar. 27, 2020 for U.S. Appl. No. 16/594,256.
Non-Final Office Action for U.S. Appl. No. 16/096,031, dated May 8, 2020.
Non-Final Office Action for U.S. Appl. No. 16/183,162, dated May 13, 2020.
Non-Final Office Action for U.S. Appl. No. 16/169,334, dated May 8, 2020.
Non-Final Office Action for U.S. Appl. No. 16/183,171, dated May 13, 2020.
PCT International Search Report and Written Opinion for International Patent Appln. No. PCT/US2019/050467, dated Dec. 18, 2019 (17 pages).
Foreign OA for Japanese Patent Application No. 2018-535810 dated Feb. 7, 2020.
Extended European Search Report for EP Patent Appl. No. 20185092.2 dated Sep. 11, 2020.
EP Examination Report for EP Patent Appl. No. 18745794.0 dated Jul. 20, 2020.
Amendment Response to Non-Final Office Action for U.S. Appl. No. 16/183,171, dated Jul. 30, 2020.
Amendment Response to Non-Final Office Action for U.S. Appl. No. 16/183,162, dated Jul. 30, 2020.
Applicant Interview Summary for U.S. Appl. No. 16/096,031, dated Jul. 30, 2020.
Applicant Interview Summary for U.S. Appl. No. 16/169,334, dated Jul. 30, 2020.
Applicant Interview Summary for U.S. Appl. No. 16/183,133, dated Aug. 24, 2020.
Non-Final Office Action for U.S. Appl. No. 16/183,149, dated Aug. 18, 2020.
Amendment Response to NFOA for U.S. Appl. No. 16/183,149, dated Sep. 25, 2020.

* cited by examiner

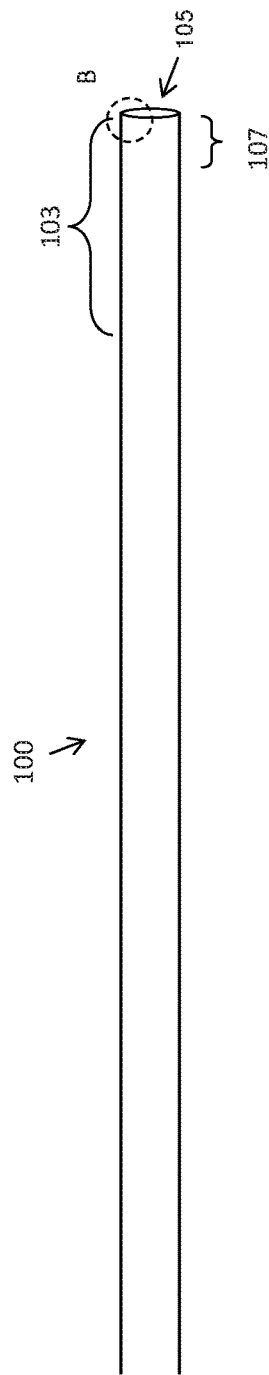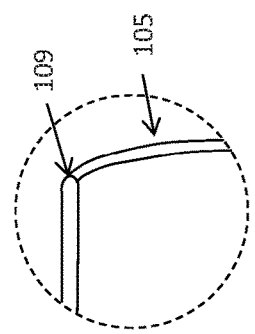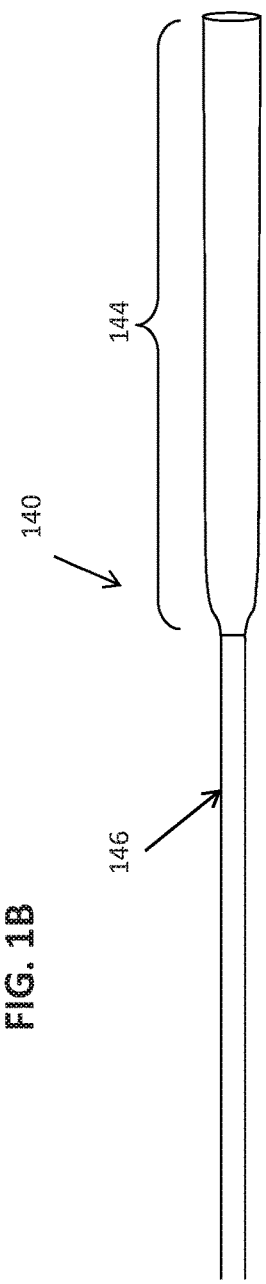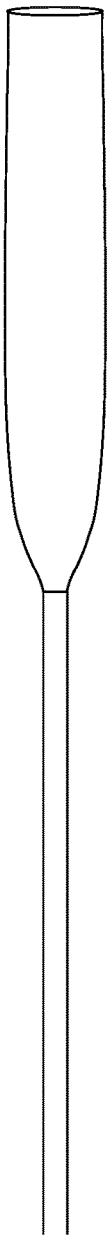
FIG. 1A
FIG. 1B
FIG. 1C
FIG. 1D

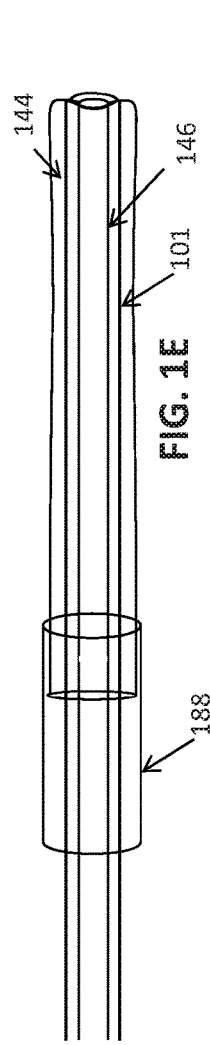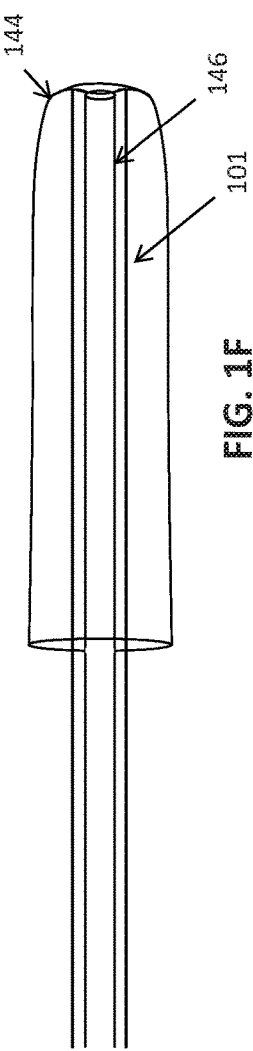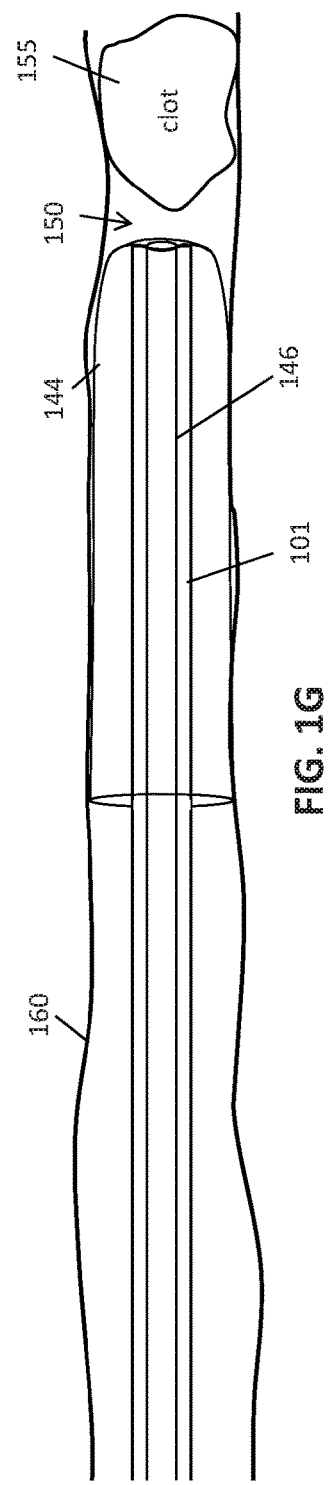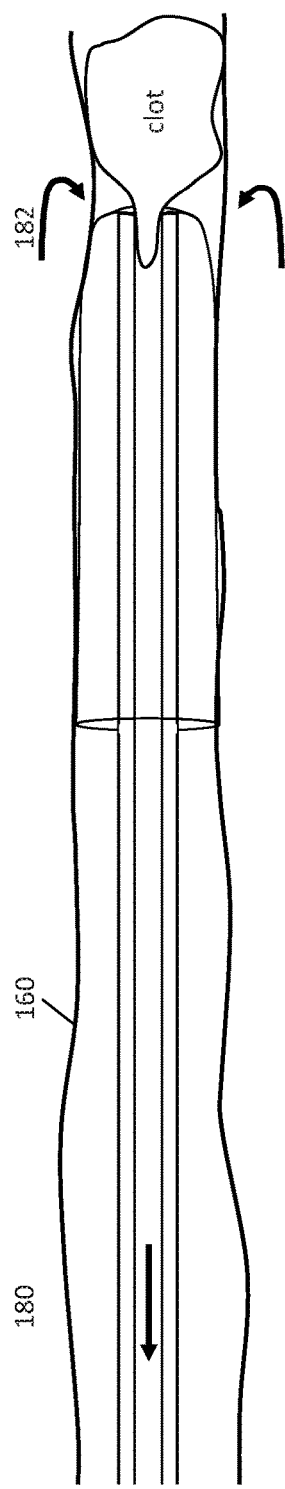

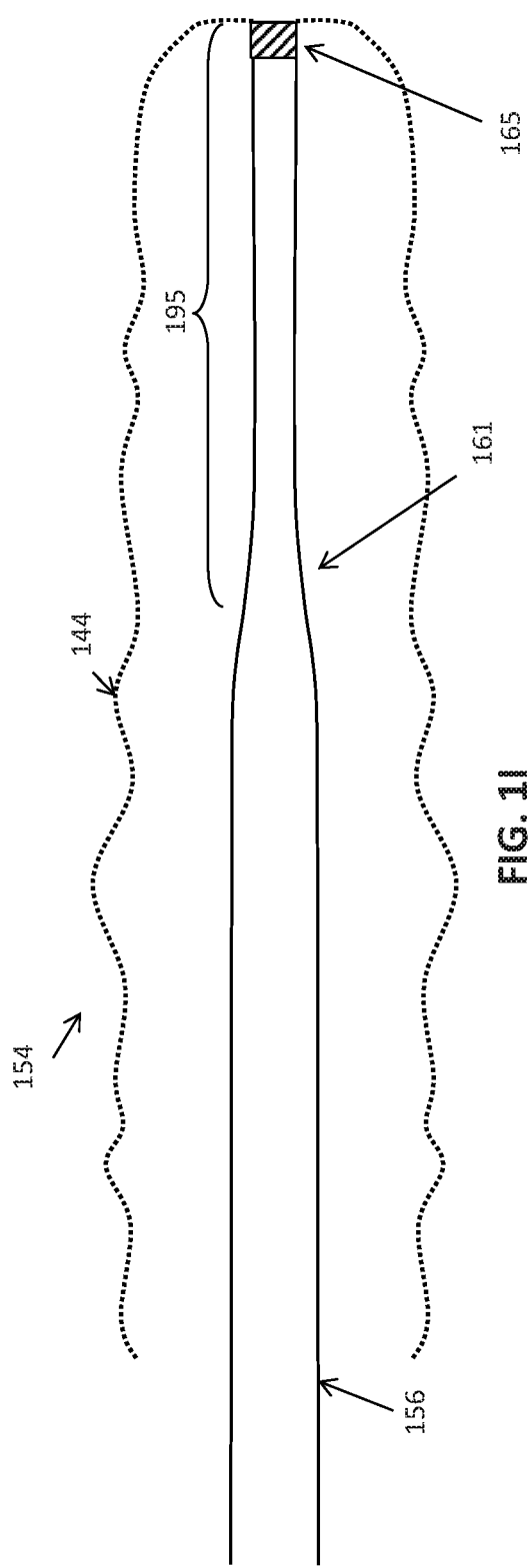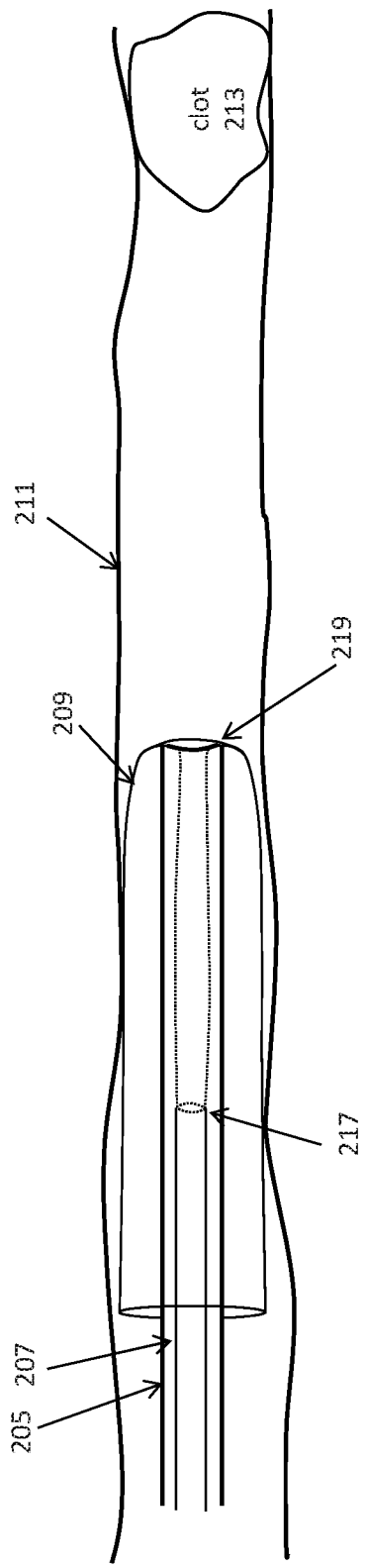

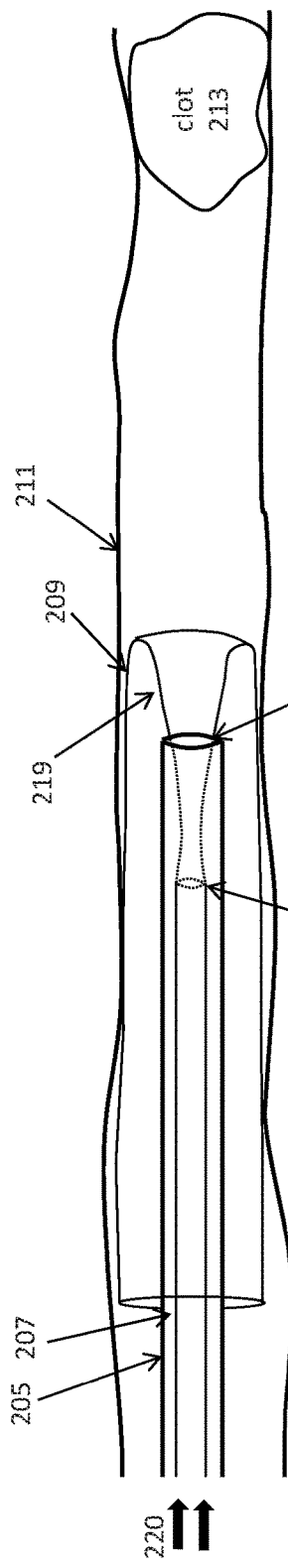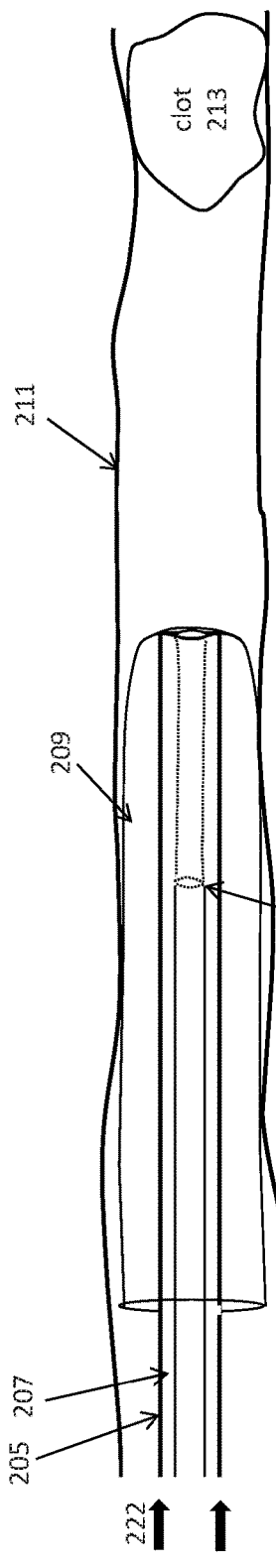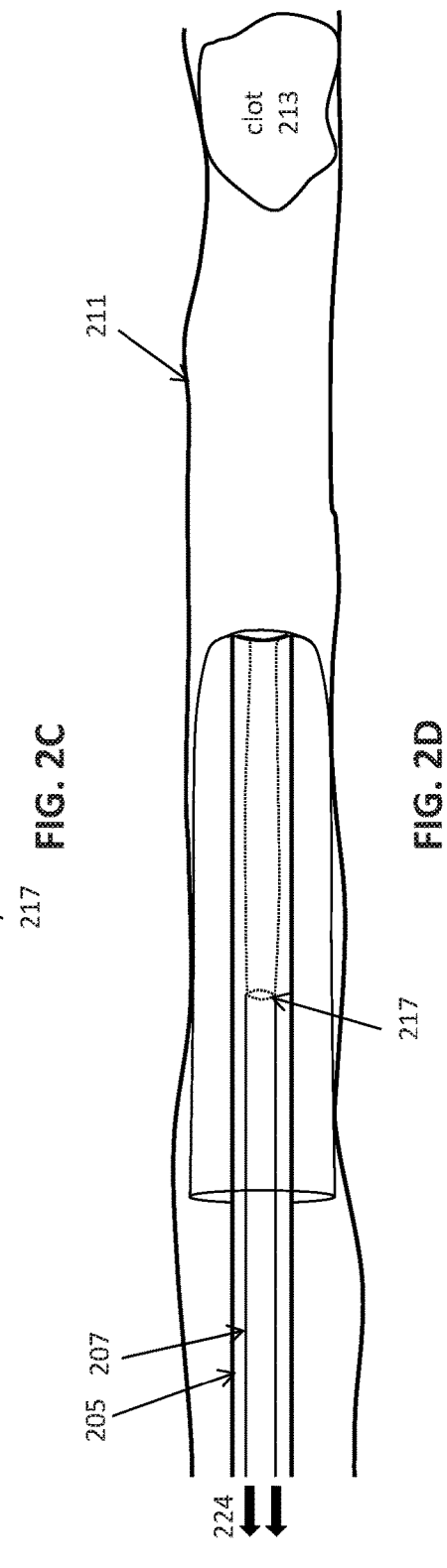

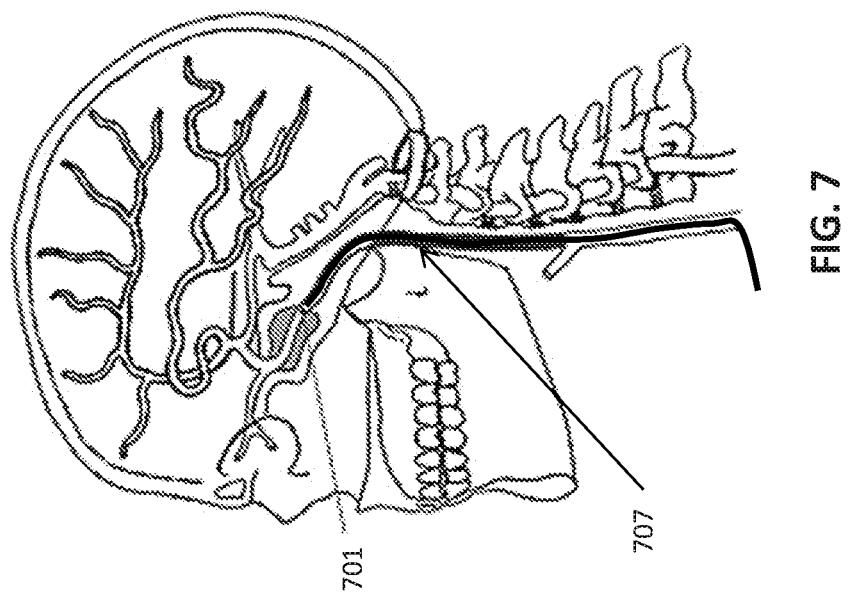

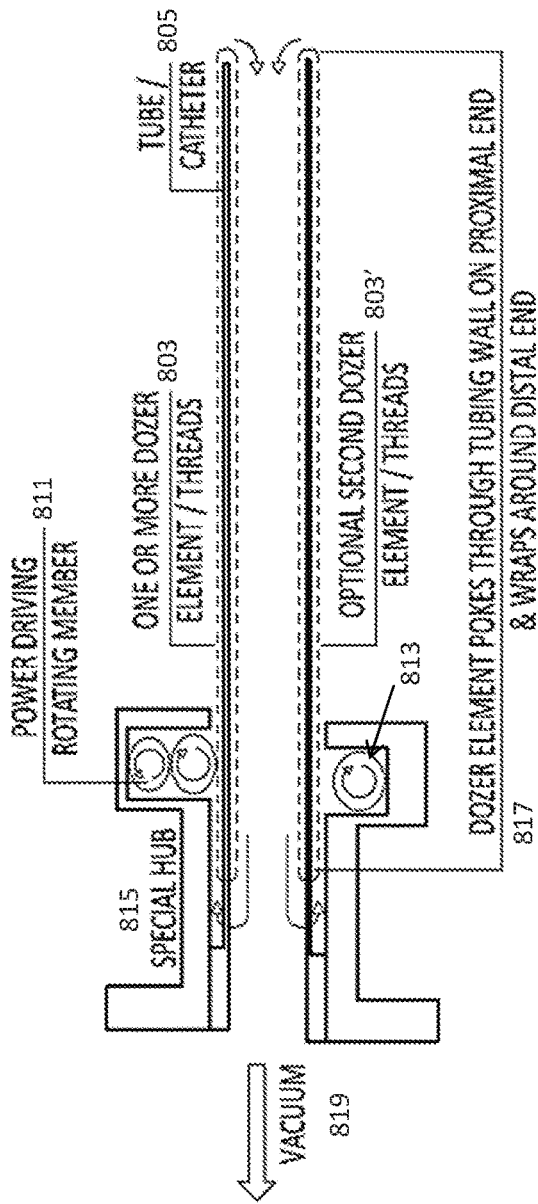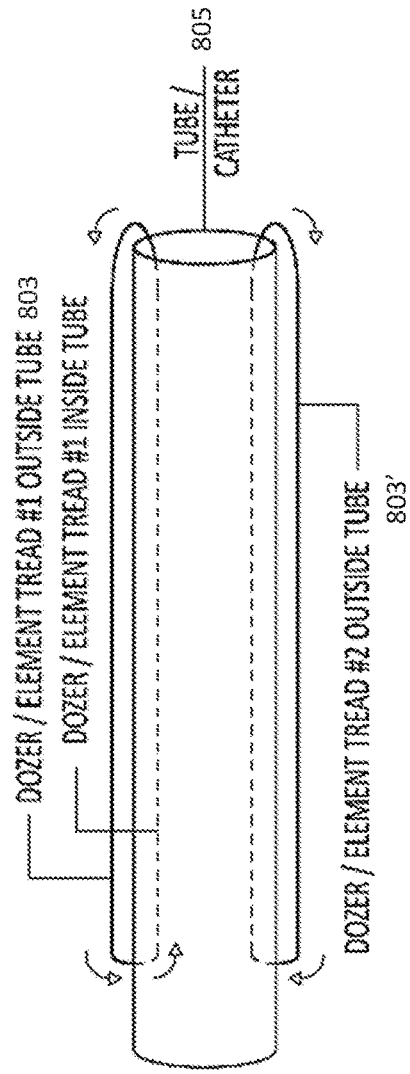

METHODS FOR ADVANCING INVERTING MECHANICAL THROMBECTOMY APPARATUSES IN THE VASCULATURE

CROSS REFERENCE TO RELATED APPLICATIONS

This patent application is a divisional of U.S. patent application Ser. No. 15/496,786, filed Apr. 25, 2017, which claims priority to U.S. provisional patent application No. 62/327,024, filed on Apr. 25, 2016 and titled "DOZER THROMBECTOMY SYSTEM."

This patent application may be related to U.S. patent application Ser. No. 15/291,015, filed on Oct. 11, 2016, titled "MECHANICAL THROMBECTOMY APPARATUSES AND METHODS", which is a continuation of U.S. patent application Ser. No. 15/043,996, filed Feb. 15, 2016, now U.S. Pat. No. 9,463,035, which claims priority to each of the following provisional patent applications: U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical thrombectomy apparatuses and methods.

BACKGROUND

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are apparatuses (devices, systems and kit) and methods of using them that may address the needs and problems discussed above.

SUMMARY OF THE DISCLOSURE

Described herein are mechanical thrombectomy apparatuses (devices, systems, etc.) and methods for using them to remove a thrombus, e.g., clot, from within a vessel. These mechanical thrombectomy apparatuses may be inverting tractor thrombectomy apparatuses. Typically, the mechanical thrombectomy apparatuses described herein are inverting tractor thrombectomy apparatuses that includes a tractor (e.g., tractor region, tractor portion, etc.) comprising a flexible tube of material that inverts over itself as it rolls over a distal end opening of an elongate inversion support. The elongate inversion support typically comprises a catheter having a distal end opening into which the tractor inverts. The flexible tractor inverts and rolls back into itself and may be drawn into the elongate inversion support in a conveyor-like motion; the outward-facing region rolls around to become an inward-facing region, e.g., within the lumen of the elongate inversion support. The rolling motion may thus draw a clot or other object within a vessel into the elongate inversion support.

Before these apparatuses can remove a clot from a vessel, however, they must be positioned within the vessel adjacent to the clot to be removed. As described herein, the inverting tractor thrombectomy apparatuses described herein may be accurately positioned either with our without the use of a guidewire or guide sleeve within a vessel by taking advantage of the rolling motion of tractor at the distal end of the apparatus. The arrangement of the tractor, elongate inversion support (e.g. which may be or may include a catheter) and the puller connected to the tractor may be used to easily and accurately position the apparatus adjacent a clot and remove the clot in a manner that may be both easier and more efficient than other methods.

Described herein are methods of advancing an inverting tractor thrombectomy apparatus forward in the vasculature. These systems and methods may use the rolling motion of the tractor to move through the vasculature including over/around clot.

For example, described herein are methods of removing a clot from a vessel using a mechanical thrombectomy apparatus. The mechanical thrombectomy apparatus may include an elongate inversion support (comprising or consisting of a catheter) that extends in a long axis from a proximal end to a distal end, a puller extending distally within the elongate inversion support (e.g. catheter) and a flexible and tubular tractor, wherein the tractor is coupled to a distal end region of the puller and further wherein the tractor is inverted over a distal end opening of the catheter so that the tractor extends proximally over the catheter. Any of these methods may include: advancing the puller distally within the elongate inversion support (e.g., catheter) and within the vessel towards a clot, so that the tractor extends from the puller distally beyond the distal end opening of the catheter, forming a gap between the tractor and the distal end opening of the catheter; advancing the catheter distally over the puller and into the gap; and drawing the clot into the catheter with the tractor by pulling the tractor proximally within the catheter so that the tractor rolls and inverts over the distal end opening of the catheter.

Any of these methods may include repeating the advancing steps one or more times. For example the method may include: advancing the puller distally within the elongate inversion support (e.g., catheter) and within the vessel towards a clot, so that the tractor extends from the puller distally beyond the distal end opening of the catheter, forming a gap between the tractor and the distal end opening of the catheter; advancing the catheter distally over the puller and into the gap; repeating the advance steps until the distal end opening of the catheter is adjacent to the clot; and drawing the clot into the catheter with the tractor by pulling the tractor proximally within the catheter so that the tractor rolls and inverts over the distal end opening of the catheter.

These methods for advancing the apparatus may therefore be described as "inchworm" type advancement, as the tractor is extended from within the catheter to distally extend in the vessel, then the catheter may follow the tractor distally. In any of these methods, the tractor may be 'reset' back into the catheter (as it may otherwise be left deployed out of the catheter along vessel), by pulling it back into the catheter. For example, the tractor may be pulled back into the catheter by pulling proximally on the puller once the catheter distal end opening is positioned against the distal-facing tractor (the region doubling-back or inverting over itself) so that the tractor can roll over the distal end opening. Resetting or repositioning the tractor in this manner may require that the apparatus be configured to prevent jamming (e.g., "anti-jamming"), including one or more of: having a lubricious and/or smooth tip, having a tip region that is more rigid than the more proximal regions of the tip, and/or having a tractor that is biased to have a first relaxed configuration that has an outer diameter that is greater than the inner diameter of the catheter and a second relaxed configuration that has an inner diameter that is greater than the outer diameter of the catheter, where the tractor converts between the first and second configurations by inverting over itself (e.g., over the distal end opening of a catheter). These configurations may prevent the tractor for buckling when pushed out of the distal end opening or when pulled back into the distal end opening of the catheter.

In any of the variations described herein, the repeated steps of inching forward by extending the tractor distally (e.g., pushing the puller coupled to the tractor distally, including distally out of the distal opening of the catheter), then advancing the catheter into the gap formed by the folded-over tractor, e.g., the gap between the distal end opening of the catheter and the tractor, may also include resetting the tractor by pulling the tractor back into the catheter once the distal end of the catheter has been advanced.

In any of these methods, the steps of advancing the tractor distally from the distal-end of the catheter and advancing the catheter behind the tractor (and optionally pulling the tractor back into the catheter by pulling proximally while holding the catheter fixed (or advancing it distally) may be repeated until the apparatus is adjacent to the clot; thereafter the clot can be removed as discussed above, by pulling the puller proximally to draw the tractor into the catheter.

In general, drawing the clot into the catheter may include advancing the catheter distally while pulling the pusher proximally.

In any of the methods described herein, the apparatus may be advanced distally (or retracted proximally) without the use of a guidewire or guide catheter. For example, advancing the puller distally may comprise advancing the puller without using a guidewire extending distal to the puller.

As mentioned, advancing the puller may comprise extending the distal end of the puller out of the distal end opening of the catheter. Alternatively the puller may remain in the catheter when advanced distally.

The tractor may be any appropriate tractor, including a woven, braided, or knitted tractor, or a tractor formed of a solid sheet of material (e.g., that may be cut or perforated). For example, advancing the puller may comprise extending the tractor distally within the vessel, further wherein the tractor comprises a woven flexible and tubular tractor. Advancing the puller may comprise extending the tractor distally within the vessel, further wherein the tractor comprises a knitted tractor.

Any of the methods described herein may include using a puller and tractor having a lumen (e.g., central lumen) through which a guidewire may be advanced. For example, advancing the puller may comprise extending the tractor distally within the vessel, further wherein the puller comprises a central lumen configured to pass a guidewire therethrough.

Further, any of the methods described herein may be performed in any vessel within the body, including peripheral and neurovascular vessels. For example, any of these methods may be performed within an internal carotid artery (e.g., advancing the puller may comprise advancing the puller within an internal carotid artery).

Also described herein are methods of positioning a mechanical thrombectomy apparatus within a vessel and/or removing a clot from a vessel using the mechanical thrombectomy apparatus in which the mechanical thrombectomy apparatus includes a puller within a first catheter that is within a second catheter, wherein the puller and second catheter are connected by a flexible and tubular tractor. For example, the method may comprise: advancing the puller distally through the first catheter and the second catheter and within the vessel towards a clot, so that the flexible and tubular tractor extends from the puller beyond a distal end opening of the first catheter and beyond a distal end opening of the second catheter; advancing the outer catheter distally through the vessel by one or more of: holding the position of the first catheter within the vessel and pulling the puller proximally within the first catheter; or moving the first catheter distally relative to the puller; and drawing the clot into the first catheter with the flexible and tubular tractor by pulling the flexible and tubular tractor proximally within the first catheter so that the flexible and tubular tractor rolls and inverts over the distal end opening of the catheter. Any of these methods may also include repeating the advancing steps until the clot is adjacent to the distal end of the puller.

Drawing the clot into the catheter may further include advancing the first catheter distally while pulling the pusher proximally. Advancing the puller distally may include advancing the puller without using a guidewire extending distal to the puller. Advancing the puller may include extending the flexible and tubular tractor distally within the vessel further wherein the flexible and tubular tractor comprises a woven flexible and tubular tractor. Alternatively, advancing the puller may include extending the flexible and tubular tractor distally within the vessel further wherein the flexible and tubular tractor comprises a knitted flexible and tubular tractor.

As mentioned, advancing the puller may comprise extending the flexible and tubular tractor distally within the vessel further wherein the puller has a central lumen configured to pass a guidewire therethrough.

In any of these methods, drawing the clot into the first catheter may comprise uncoupling the flexible and tubular tractor from the second catheter.

Also described herein are mechanical thrombectomy apparatus for removing a clot from a vessel that include a motorized or motor-driven tractor. For example described herein are apparatuses including: a flexible catheter having a distal end and a distal end opening; a tractor comprising a flexible belt that extends within the catheter, inverts over the distal end opening of the catheter and extends along the outer diameter of the catheter; a power drive at a proximal end of the flexible catheter configured to drive the tractor around the catheter so that it inverts over the distal end opening of the catheter; and a guidewire lumen through the catheter and the tractor configured to pass a guidewire.

The flexible belt may comprise a flexible tube. In some variations, the tractor comprises a plurality of flexible belts that each extend within the catheter, invert over the distal end opening of the catheter and extend along the outer diameter of the catheter.

The power drive may be configured to engage with the flexible belt on an outer surface of the catheter. The power drive may comprise an annular ring surrounding the catheter and the tractor.

Any of these apparatuses may include an outer catheter configured to enclose the flexible catheter and tractor, wherein the flexible catheter and tractor may be inserted through the body within the outer catheter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1H illustrate an example of a mechanical thrombectomy apparatus for mechanically removing an object such as a clot form a body region. FIG. 1A shows an example of an elongate inversion support portion of an apparatus, configured as a catheter. For example, at least the distal end of the elongate inversion support may be configured as a catheter. FIG. 1B shows an enlarged view of a distal end (opening) of the catheter of the elongate inversion support of FIG. 1A, showing the aperture formed by the distal end opening; FIG. 1C shows an example of a distal tractor region of a flexible tube (tractor tube) extending from a puller (the puller in this example is configured as a catheter. The tractor is shown in a first (e.g., un-inverted) configuration) and may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. 1E. In FIG. 1E, the assembled mechanical thrombectomy apparatus with the elongate inversion support and the flexible tube forming the tractor is shown. The tractor extends through the catheter of the elongate inversion support and doubles back over the distal end opening of the catheter and extends over the outer diameter of the catheter. The outer portion of the tractor (extending along the outer diameter of the catheter) may be held in a collapsed configuration (as shown in FIG. 1E), or it may be expanded, as shown in FIG. 1F. Thus, the tractor may be biased so that in the second configuration (inverted over the distal end of the catheter), the tractor has a 'relaxed' outer diameter that is greater than the outer diameter of the catheter of the elongate inversion support. FIGS. 1G and 1H illustrate the use of the apparatus of FIGS. 1E and 1F to remove a clot by drawing the flexible tube proximally and/or advancing the catheter distally towards the clot so that the expandable first end region inverts as it is drawn into the distal end of the catheter, pulling the clot into the catheter.

FIG. 1I illustrates an alternative variation of a tractor and puller. In FIG. 1I, the tractor is shown attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

FIGS. 2A-2E illustrate a method of positioning a mechanical thrombectomy apparatus within a vessel and/or removing a clot from a vessel using the mechanical thrombectomy apparatus. In FIGS. 2A-2E the apparatus is shown inching distally within the vessel towards the clot using the tractor, so that the clot may be captured and removed by the tractor. In FIGS. 2A-2E the apparatus is advanced distally without the use of a guidewire.

FIG. 7 illustrates one region (e.g., the internal carotid artery) in which the apparatuses and methods described herein may be used.

FIG. 8A-8B illustrate an example of a mechanical thrombectomy apparatus for removing a clot from a vessel that include a motorized or motor-driven tractor. FIG. 8A shows the apparatus in a side view, schematically illustrating the internal components. FIG. 8B is an example of a catheter and tractor(s) that may be used with an apparatus such as the one shown in FIG. 8A.

DETAILED DESCRIPTION

Figure 2E:
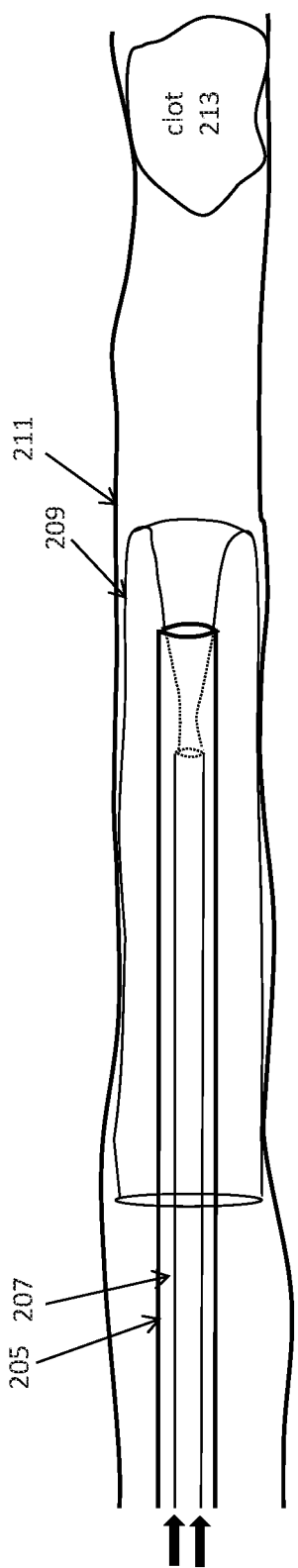
Figure 3A:
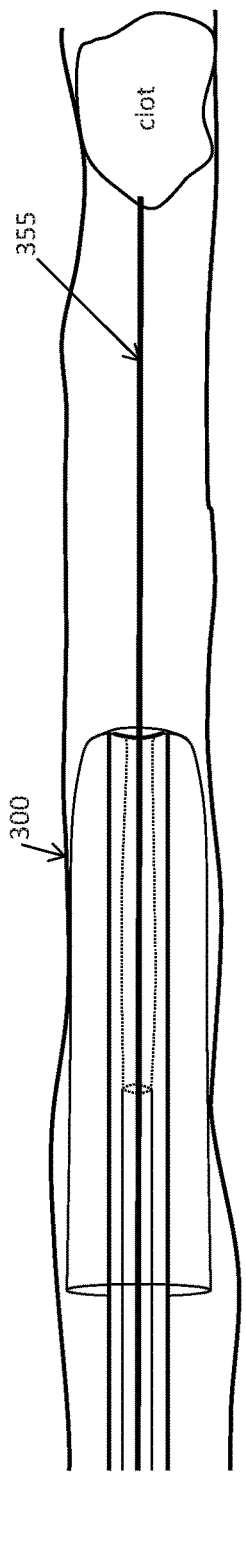
FIGS. 3A-3D illustrate a method of positioning a mechanical thrombectomy apparatus within a vessel and/or removing a clot from a vessel using the mechanical thrombectomy apparatus similar to that shown in FIGS. 2A-2E only using a guidewire.
Figure 3B:
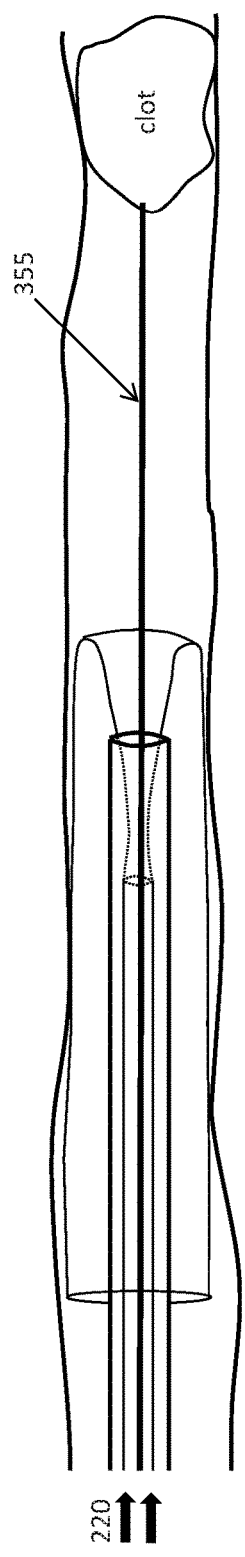
Figure 3C:
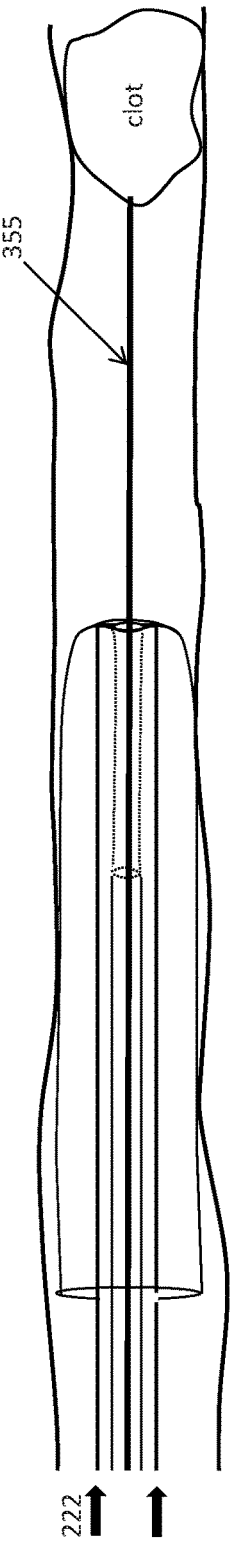
Figure 3D:
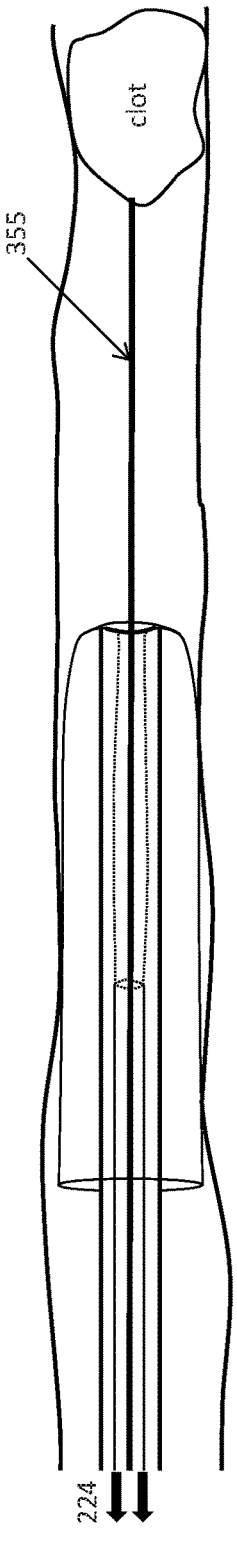

Described herein are mechanical thrombectomy apparatuses, including manually drive and power-driven apparatuses, and methods of using them. In particular, described herein are methods of positioning these apparatuses within a vessel and/or removing clot with them that may include extending the tractor region and/or the puller distally of the distal end of the apparatus to assist in advancing the apparatus distally.

Any of the mechanical thrombectomy apparatuses described herein may have an inverting tractor that is configured to prevent jamming and grab a blood clot. These apparatuses may include an elongate elongate inversion support that supports an annulus over which the tractor inverts at the distal end. The tractor may comprise a flexible tube that doubles back over (e.g., inverts) over the distal end of the elongate inverting support (e.g., a catheter) so that it extends into the annuls opening of the elongate inverting support and an inner puller coupled to the inner end of the tractor that the tractor can be pulled proximally to pull and invert the tractor over the annulus at the distal end of the elongate inverting support to roll and capture a clot. The apparatus may include a guidewire lumen extending through the elongate inverting support, and/or tractor puller that is configured to pass a guidewire.

The apparatuses described herein may be adapted to prevent jamming, e.g., by including a coating (e.g., hydrophilic, lubricious coating, etc.) or the like to enhance the sliding and inverting of the tractor over the distal end. Further, any of these apparatuses may include one or more projections that are configured to enhance grabbing and/or maceration of a clot. Grabbing of a clot may be particularly, but not exclusively, helpful when the tractor is lubricious. Although lubricious tractors may resist jamming and require less force to operate, e.g., inverting over the distal end of the catheter, it may be more difficult to initially grab or grasp clot when the tractor is more lubricious. It may also be particularly helpful to include projections that are retracted along the length of the tractor adjacent to the outer diameter of the elongate inverting support (e.g., catheter), for example, when positioning the apparatus within a vessel, but extend the projections outward from the tractor when rolling and inverting to grab a clot.

In general, a mechanical thrombectomy apparatus for removing a clot from a vessel may be a system, assembly or device including an elongate inversion support having a distal end and a distal annulus, and a flexible tractor assembly at least partially inverted and configured to roll and invert over the distal annulus of the elongate inverting support.

In many of the examples described herein, the elongate inversion support is a catheter (or a portion of a catheter at the distal end) and the annulus is formed by the distal end opening of the catheter; the tractor extends within the catheter and doubles back over the distal end of the catheter to extend over the outer diameter of the catheter at the distal end of the catheter, although it may extend proximal for any appropriate distance (including between 1-30 cm, between 2-20 cm, greater than 1 cm, 2 cm, 3 cm, 4 cm, 5 cm, 6 cm, 7 cm, 8 cm, 9 cm, 10 cm, 11 cm, 12 cm, 15 cm, 20 cm, etc.). The end of the tractor within the catheter may be coupled to a puller (e.g., at a proximate puller region connected to the distal or inner end of the tractor). The tubular tractor may include an elongate lumen that is configured to allow passage of a guidewire. The tubular tractor may also be configured to slide along the long axis within the catheter lumen and invert over the distal end opening of the catheter when the proximal end region is pulled proximally. The tractor may be referred to herein as a tractor assembly, tractor portion, tractor tube, or simply a tractor, and is typically positioned and longitudinally slideable within the catheter, and arranged so a portion of the tractor (sometimes referred to as the "distal tractor region" or "distal-facing" tractor region) doubles back over itself.

For example, FIG. 1A shows one variation of a catheter of an elongate inversion support that may form part of the apparatuses described herein. In this example, the elongate inversion support includes a catheter 100 having a distal end region 103 that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include a elongate inversion support that is not a full-length catheter, but may include a portion of a catheter, typically at the distal end, connected to a rod, wire, hypotube, or the like (as will be described in greater detail below in reference to FIGS. 42A-43D) or may be skived. Thus, any of the apparatuses and methods described herein may be adapted for use with an elongate inversion support that is not limited to catheters, including elongate inversion supports that include a portion of a catheter, or that include a ring or other structure forming the annulus at the distal end. In FIG. 1A the catheter 100 of the elongate inversion support may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end) may be curved or radiused 109 as shown in FIG. 1B, particularly on the outer surface (e.g., the transition from outer diameter to inner diameter).

FIG. 1C shows an example of a flexible tractor 144 coupled to a puller 146. In this example to form a pullable tractor assembly 140, the tractor is shown integrated with the puller, forming the assembly. In FIG. 1C, the tractor is a tube of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). In the example shown in FIG. 1C, the tractor 144 is configured, e.g., by shape-setting (heat setting, etc.), to expand in the relaxed first configuration to a radial diameter that is between 1.1 and 10 times the diameter of the inner diameter of the catheter of the elongate inversion support when unconstrained, as shown in FIG. 1D. In FIG. 1D, the tractor of FIG. 1C is shown in an expanded, relaxed, configuration. Thus the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor 144 and a less expandable (or non-expandable) proximal portion comprising the puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

In FIG. 1E, the flexible tractor of FIG. 1C is shown with the tractor doubled back over itself an over the distal end of the catheter of the elongate inversion support 101. The distal end region is collapsed down, e.g., onto the puller and the elongate inversion support, and may be held collapsed. In this example a tractor hold 188 may be used to hold the tractor collapsed down onto the outer diameter of the elongate inversion support. However, in an unconstrained or deployed configuration, as shown in FIG. 1F, the tractor in this second configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration in the first configuration (as shown in FIG. 1C) that is greater than the inner diameter (ID) of the catheter of the elongate inversion support portion of the apparatus and the relaxed expanded configuration of the second configuration (shown in FIG. 1F) inverted over the catheter has an OD that is greater than the OD of the catheter. The tractor is expandable and may be coupled to the puller. In some variations the flexible tractor and the puller may comprise the same material but the tractor may be more flexible and/or expandable, or may be connected to a push/pull wire or catheter.

FIGS. 1G and 1H illustrate the removal of a clot using an apparatus such as the apparatus assembled from the components of FIGS. 1A and 1E. In this example the apparatus is configured as a thrombectomy apparatus including a catheter of an elongate inversion support 101 and a flexible tractor that extends over the distal end region of the catheter and doubles-over itself at the distal end of the catheter to invert so that the external tractor end region is continuous with an inner less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. FIG. 1I illustrates another example of a tractor assembly 154 including a tractor 144 that is coupled to a puller 156. The puller in this example is tapered (having tapering region 161) and may therefore have a different flexibility of the distal end region than the proximal end region. For example the proximal end region may be less flexible than the narrower-diameter distal end region 195 to which the tractor is coupled. The assembly includes a radiopaque marker 165. The tractor may be attached to the puller by any appropriate means. For example, the tractor may be crimped, glued, fused, or otherwise attached to the puller, typically permanently.

In general the mechanical thrombectomy apparatuses described herein may be highly flexible, both before actuating and during operation. For example, the flexible tractor may not increase the stiffness/flexibility of the catheter of the elongate inversion support, and particularly the distal end region of the catheter too much, to avoid impacting maneuverability, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

Methods of Advancing an Inverting Tractor Apparatus

A mechanical thrombectomy apparatus may be advanced distally within a vessel and may grab and engulf a clot that is located distally by using the tractor to extend distally ahead of the apparatus, and in some cases pull (e.g., against the vessel walls) to guide or draw the catheter distally forward. This method of advancement may be referred to as "inchworm" or 'worm-like" motion within the vessel. For example, FIGS. 2A-2E illustrate a first method of advancing a mechanical thrombectomy apparatus and/or removing a clot from a vessel using the mechanical thrombectomy apparatus. In this example, the apparatus includes a catheter 205 extending proximally to distally, a puller 207 (shown as a thin tube or hypotube, though it may be a wire or rod, as mentioned above), extending distally within the catheter and a flexible and tubular tractor 209. The tractor is coupled to a distal end region of the puller 217 and the tractor is inverted over a distal end opening of the catheter 219 so that the tractor extends proximally over the outside (outer diameter) of the catheter. In operation, the apparatus may be advanced distally (e.g., towards a clot 213) in a vessel 211, as shown in FIGS. 2B-2D. In FIG. 2B, the puller is pushed distally 220 (shown by arrows on the left) to advanced distally within the catheter and within the vessel towards a clot, so that the tractor extends from the puller distally beyond the distal end opening of the catheter 218, forming a gap 219 between the tractor and the distal end opening of the catheter. This gap is an annular, distal-facing cavity (e.g. pouch) formed in the tractor, and into which the distal end opening of the catheter may be advanced, as shown in FIG. 2C. In FIG. 2C, the catheter is advanced distally over the puller and into the gap. Following this step, the tractor is extended further outside of the catheter, and is in contact with the walls of the vessel 211, through it does not have to be. The outer diameter of the expanded tractor maybe narrower than the vessel inner diameter (ID) or it may be greater than then ID of the vessel (and may therefore touch against them.

When advancing the catheter distally 222 (shown in arrows on left) and into the gap, the puller may be held in position relative to the catheter. In variations in which the tractor contacts the outer diameter of the vessel, this contact may hold the tractor in place against the vessel wall.

The steps of FIGS. 2B and 2C may be repeated multiple times to continue to advance the apparatus distally, however, in some variations it may be beneficial to retract or reset the tractor back into the catheter, e.g., by withdrawing the puller proximally to pull the tractor back into the catheter. This is illustrated in FIG. 2D. In this example, the puller 207 is withdrawn proximally 224 (arrows on left), so that the tractor coupled to the puller 217 is pulled back into the catheter after inverting over the distal end opening of the catheter. It may be beneficial to perform this step after the catheter has been extended distally fully, e.g., until it pushes distally against the back of the inverting (bent-over) region, as shown in FIG. 2D. One the tractor has been sufficiently retracted, the steps shown in FIGS. 2B-2C may be repeated, as shown in FIG. 2E, until the distal end opening of the catheter is adjacent to the clot. After positioning next to the clot (and in some cases adjacent to it), vacuum may be applied to pull the clot into contact with the apparatus, and/or the device may be advanced by pushing the catheter distally while pulling the puller proximally to roll and invert the tractor into the catheter (see., e.g., FIG. 1H).

The method of advancing the apparatus described in FIGS. 2A-2E above may be particularly helpful in advancing the apparatus within a vessel even without the use of a guidewire or equivalent (e.g., guide catheter). However this method may also be used with a guidewire, as illustrated in FIGS. 3A-3D. In this example, the apparatus 300 is otherwise the same as shown in FIGS. 2A-2E, but may include or be used with a guidewire 355. In general, the same steps may be performed as discussed above. Alternatively, before or after a cycle of inching forward as describe in FIGS. 2A-2E, the apparatus may be slid distally along the guidewire toward the clot. Thus, in some variations, this method may be used to help navigate the apparatus within congested or tortious regions where advancing by sliding may not be as effective.

Another method of advancing an apparatus distally using the tractor is illustrated in FIGS. 4A-4D. This method is also similar to that shown in FIGS. 2A-2E and 3A-3C above, but may extend the tractor portion even further distally using the pusher, so that the pusher extends past the distal end of the apparatus, out of the catheter. In contrast, in FIGS. 2A-2E, the pusher remains substantially within the catheter, thus smaller 'steps' may be taken by the device.

Figure 4A:
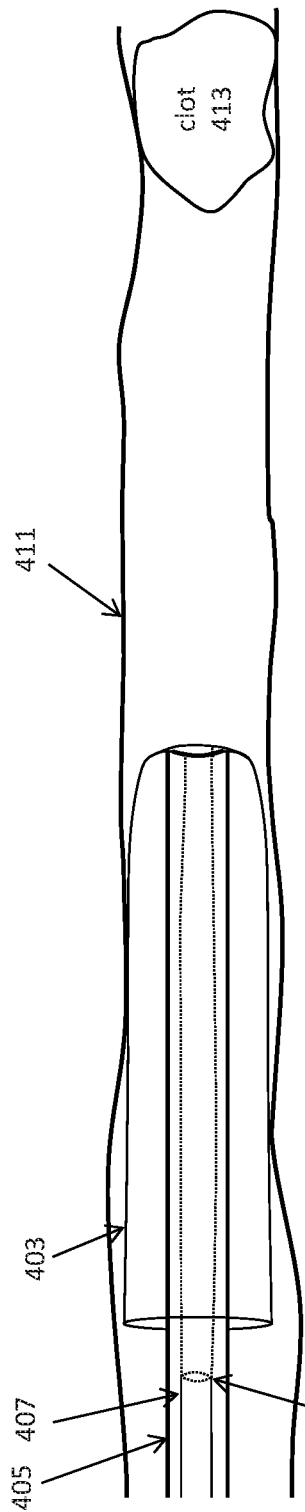
FIGS. 4A-4D illustrate a method of positioning a mechanical thrombectomy apparatus within a vessel and/or removing a clot from a vessel using the mechanical thrombectomy apparatus in which the distal end of the puller, to which one end of the tractor is attached, is extended distally from the catheter.
Figure 4B:
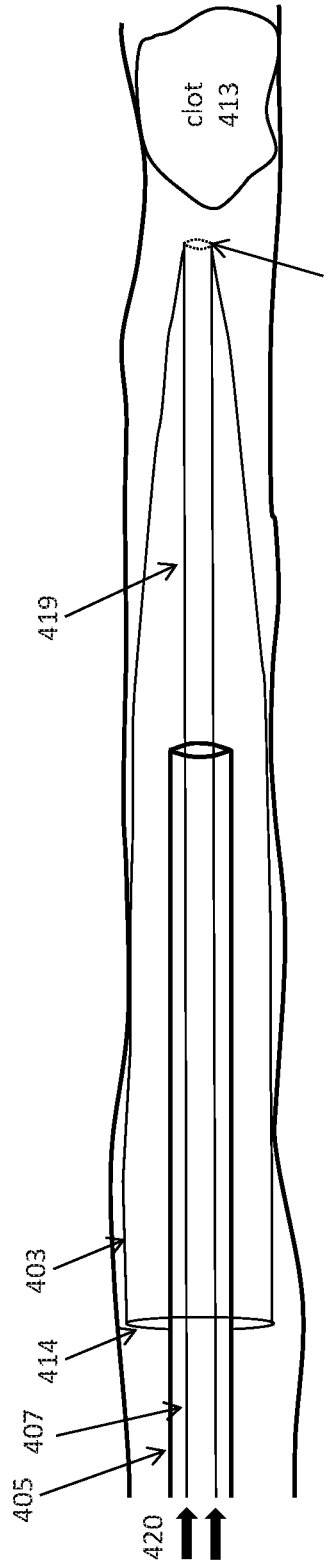
Figure 4C:
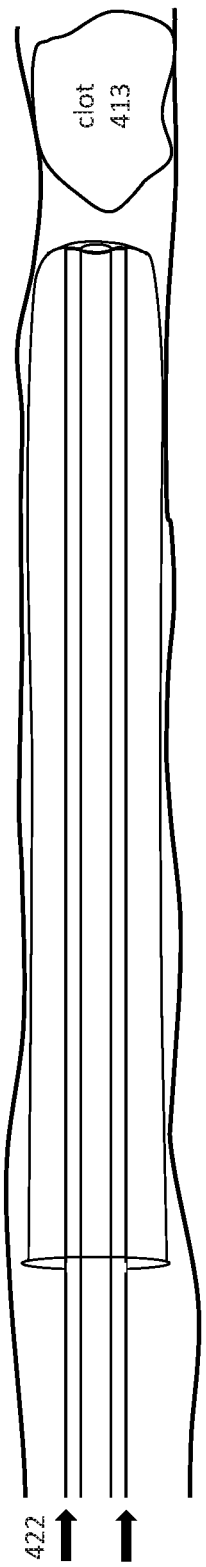

In FIG. 4A, the apparatus is similar to that discussed above, including a puller 407 that is connected at a distal end region 417 to a tractor 403. The tractor is inverted over the distal end opening of a catheter 405. The apparatus may be advanced within a vessel 411 towards a clot 413, as shown in FIG. 4B, by advancing the inner puller 407 distally 420 so that the puller distal end (and attached tractor) extends distally from the catheter distal end opening. The tractor may tent, forming a gap 419 or pouch between the distal end of the catheter and the distal face of the tractor (distal-facing end). In this example, the gap 419 is formed between the distal end of the catheter and the end of the puller. Thereafter, as shown in FIG. 4C, the catheter may be advanced distally 422 within the gap of the tractor. In both this example and the example shown in FIGS. 2A-2E, the puller and tractor may be advanced distal of the catheter distally while the outer portion of the tractor remains over the catheter, e.g. the second end of the tractor 414 that is shown extended over the outer diameter of the catheter remain proximal to the distal end of the catheter. Once positioned near the clot 413, the tractor may be rolled into the catheter by pulling proximally on the puller and (optionally) advancing the apparatus distally by pushing the catheter distally.

Figure 4D:
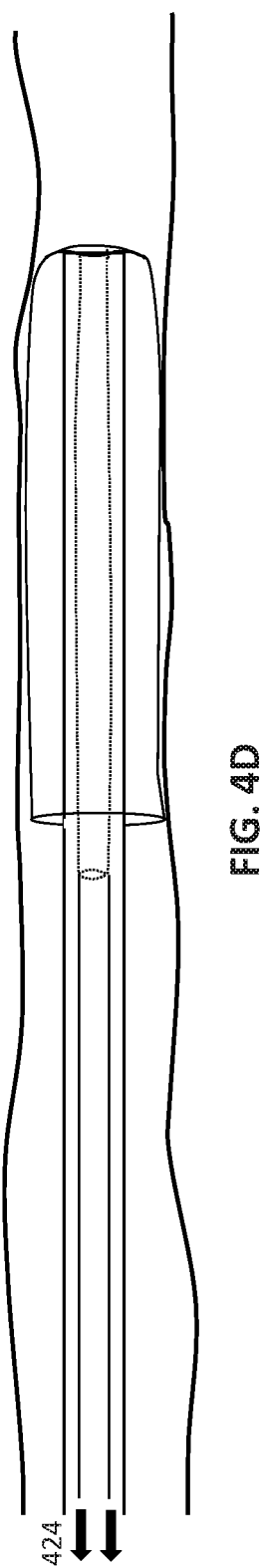

If the distal end of the apparatus (e.g., the distal-facing, inverting tractor) is not adjacent to the clot 413, the steps above can be repeated, either with or without retracting the tractor into the catheter (e.g., by pulling proximally on the puller). FIG. 4D illustrates an example of retracting the tractor into the catheter by pulling proximally on the puller 424.

Figure 5A:
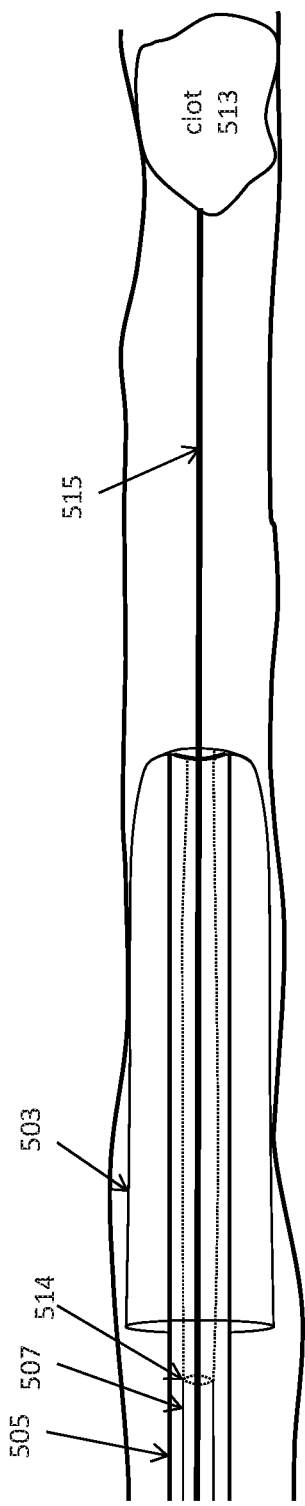
FIGS. 5A-5C illustrate a method of positioning a mechanical thrombectomy apparatus within a vessel and/or removing a clot from a vessel using the mechanical thrombectomy apparatus similar to that shown in FIGS. 4A-4D but include the use of a guidewire.
Figure 5B:
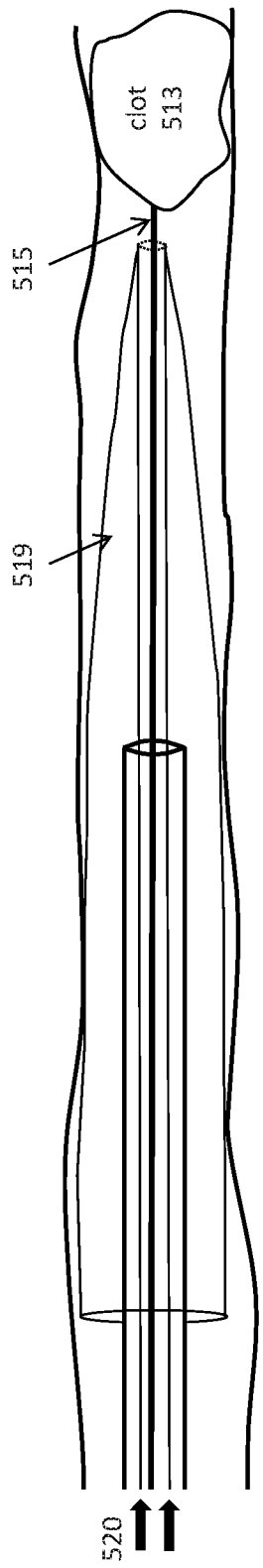
Figure 5C:
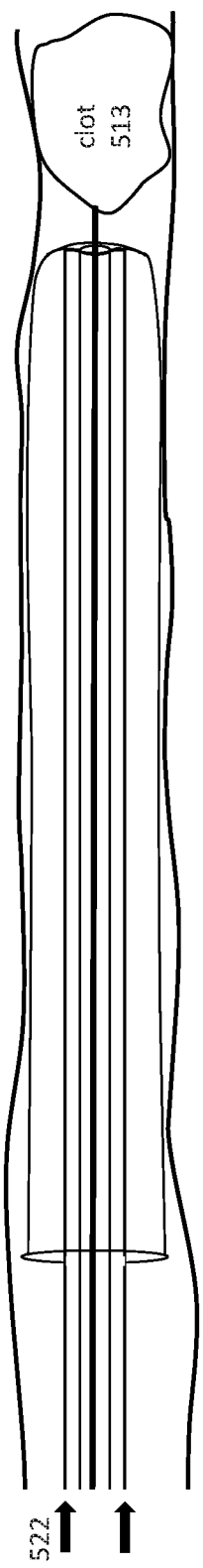

FIGS. 5A-5C illustrate the method of FIGS. 4A-4C with a guidewire 515. The apparatus may be the same (e.g., may include a puller 507 coupled at a distal end 517 to a flexible tractor 503 that is inverted over the distal end opening of a catheter 505 and extending along the outer surface of the catheter). The steps may be the same as discussed above, including advancing the tractor and puller distally by pushing the puller distally 520 towards a clot 513, as shown in FIG. 5B. The catheter may then be advanced (by sliding over the guidewire) as shown in FIG. 5C into the gap or pouch formed by the tractor 519. Once positioned near the clot 513, the tractor may be rolled into the catheter by pulling proximally on the puller and (optionally) advancing the apparatus distally by pushing the catheter distally.

Figure 6A:
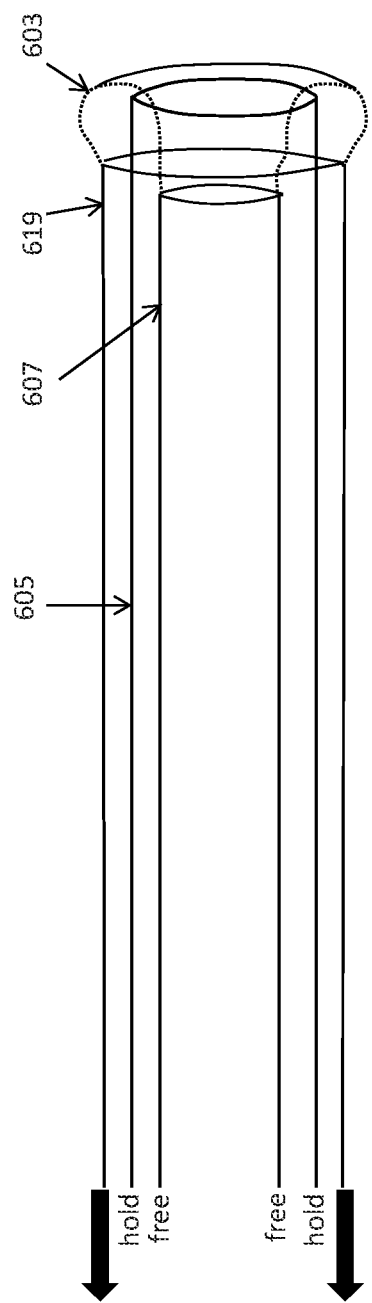
FIGS. 6A-6B illustrates another method of positioning a mechanical thrombectomy apparatus within a vessel and/or removing a clot from a vessel using the mechanical thrombectomy apparatus, in which the apparatus include a tractor that is connected (attached) to both the pusher and an outer catheter or element.
Figure 6B:
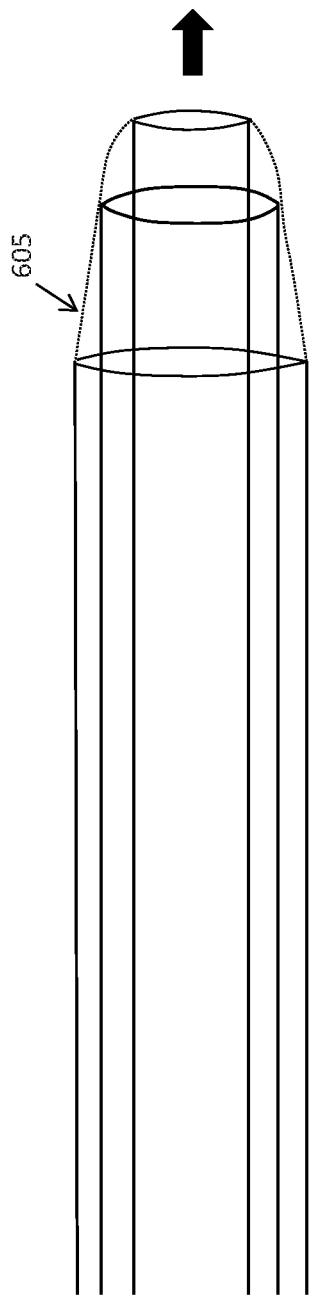

FIGS. 6A-6B illustrate another method for advancing an apparatus distally, in which both ends of the tractor 603 are coupled to axially movable elements. For example, in FIG. 6A the first end of the tractor 603 is coupled to a puller 607 within the catheter 605. In addition, the second end of the tractor is shown coupled to an outer axially movable member (second or outer catheter 619). This tri-axial system may be used to inchworm the apparatus distally by alternately holding and pulling on the various pullers and catheters. For example, in FIG. 6A, the tip of the apparatus may be advanced distally toward a clot by holding the catheter fixed, allowing the puller to float (e.g., not constraining it) and pulling the outer catheter proximally 640. As a result, the outer portion of the flexible tractor may be pulled proximally, pulling the puller and opposite end of the tractor distally, as shown in FIG. 6B. Thereafter, the puller may be held in place, the outer catheter may be free to move axially, and the catheter may be advanced distally into the gap formed by the tractor, which may drive the tractor distally (e.g., back to the configuration shown in FIG. 6A) and pull the outer catheter distally. These steps may be repeated as necessary. In some variations the outer catheter may be removably attached to the tractor, and the tractor may be pulled proximally to separate from the outer catheter.

A guidewire may also be used with this method. In this example, tip advancement of the apparatus may take advantage of the outer (e.g., guide) catheter stiffness (e.g., bending and column stiffness) to aid in catheter tip advancement. This may be particularly helpful in neurovascular regions, such as shown in FIG. 7.

FIG. 7 illustrate the uses of the methods described herein to advance the apparatus 701 within a neurovascular structure such as the internal carotid segment in the head. For example, the distal tip of the apparatus may be positioned at the distal tip of the internal carotid segment; once positioned, an advancement method such as one of those described herein may be used drive the apparatus distally forward towards the clot. Such a method may create a pushing force forward from the internal carotid artery without sacrificing the trackability of the apparatus or the small outer diameter of the apparatus.

The apparatuses described herein may also be used to advance other apparatuses (including catheters and tubes). For example, any of these apparatuses and methods may be used in reverse (e.g. pulling proximally on an outer portion of the catheter) to pull an apparatus within the lumen of the tractor distally for delivery at an internal vessel site.

Thus, to advance a tool (e.g., a tube, etc.) into the patient, a tractor inserted into the body (which may be advanced as descried herein, even for use without performing a thrombectomy or in addition to a thrombectomy) may be pulled from the outside of the catheter proximally (e.g., with an overtube or pull wire) to invert the tractor in the opposite direction from out of the catheter. As the tractor on the OD of the catheter is pulled proximally, it may advance a tool (e.g., tube) inside the apparatus to the target location in the patient. This mechanism could be used in a variety of applications including; passing mature clot or vessel lesion, placing an intubation system (e.g., in a throat), providing rectal or vaginal access, performing NOTES surgery, inserting a tool such as a trocar, inserting a scope into a body region (e.g., gastrointestinal region, colon, blood vessel lumen, etc.), inserting a robotic tool, crossing a calcified vessel, etc. Other applications of the apparatuses and methods of removing and/or placing material using the apparatuses described herein may include removal of tissue, such as gall bladder removal and removal of fat (liposuction). For example a cutting or ablative tool may be passed down the middle of the apparatus, through the catheter, the puller and the tractor, and extended from the distal end, where it may be used to cut tissue that may then be pulled out of the body using the tractor by pulling the tractor proximally within the catheter. Note that this method may be used to remove both the tool and/or the cut tissue. Thus, despite referring to these apparatuses as mechanical thrombectomy apparatuses herein, any of these devices may be adapted for uses not limited to thrombectomy, and may alternatively be referred to as mechanical tractor apparatuses.

Also described herein are powered mechanical thrombectomy apparatuses in which the tractor may be driven by a driver such as an electrical motor. For example, FIG. 8A illustrates an example of a power driven tractor in a mechanical thrombectomy apparatus. The apparatus may drive the tractor continuously in a loop, thus the tractor may be configured as a closed loop, belt or toroid of material that extends around a catheter. The power drive may run the apparatus in either the forward or reverse directions. In FIG. 8A, the tractor comprises a plurality of belts 803 that extend around and through the catheter 805. A drive motor 811 drives rotation of the belts. In FIG. 8A the drive motor drives a ring 813 that can therefor drive multiple belts forming the tractor or in some variations, a single torus that passes over the supporting catheter. The catheter may include holes or openings 817 into which the belts forming the tractor may reside. The belts extend along the length of the catheter 805. In this example, a hub 815 holds the proximal end of the catheter and holds the belts against the drive motor and/or drive ring that is driven by the drive motor, and may also connect to a vacuum 819.

FIG. 8B shows an enlarged view of a catheter and tractor that may be used with the apparatus shown in FIG. 8A. FIG. 8B shows the catheter 805 including a plurality of belts 803, 803' forming the tractor. The belts pass through an opening in the catheter at the proximal end, but roll over the distal end of the catheter, and extend along the outer and inner longitudinal axis.

Figure 9A:
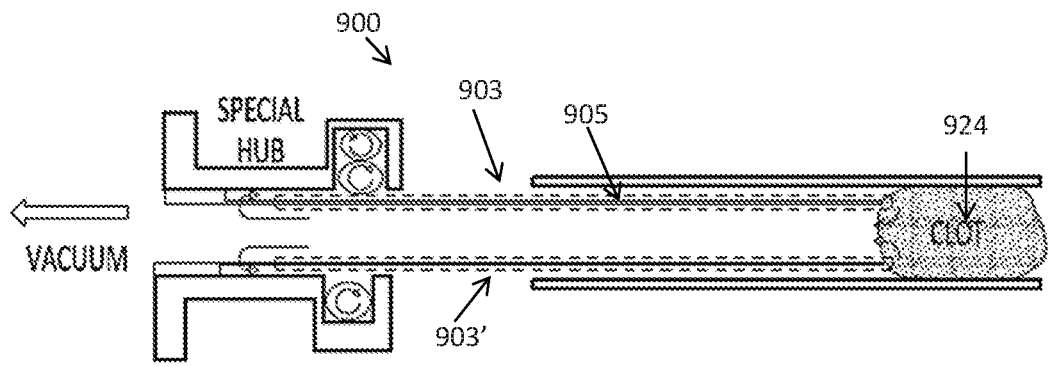
FIGS. 9A-9B illustrate a method of operating a mechanical thrombectomy apparatus for removing a clot from a vessel that include a motorized or motor-driven tractor, such as the one shown in FIGS. 8A-8B.
Figure 9B:
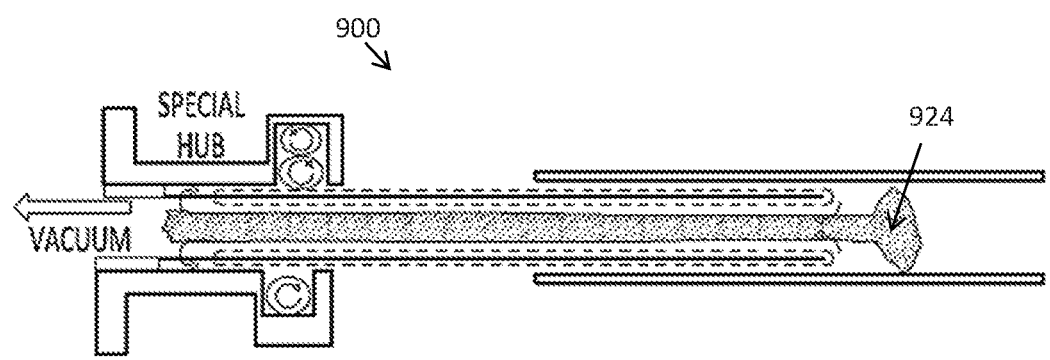

FIGS. 9A-9B illustrates an example of operation of a power driven mechanical thrombectomy apparatus configured to grab a clot. In FIG. 9A, the apparatus 900 is similar to that shown in FIG. 8A, above, including a plurality of belts 903, 903' forming the tractor, and an internal catheter 905; the bests rotate down the length of the catheter. Note that the catheter may be rigid or flexible. The catheter may include channels, and/or notches or other guide along its length for guiding and/or enclosing the belts at various portions. In FIG. 9A, the apparatus is positioned adjacent to a clot 924. The clot may initially be grabbed using aspiration (e.g., vacuum). In FIG. 9B, the apparatus may is shown after grabbing the clot, and compressing it within the catheter.

Note that the power-driven mechanical thrombectomy apparatuses shown in FIGS. 9A and 9B do not include a puller, as the motor may act like a puller. In some variations a separate puller may be used.

Figure 9C:
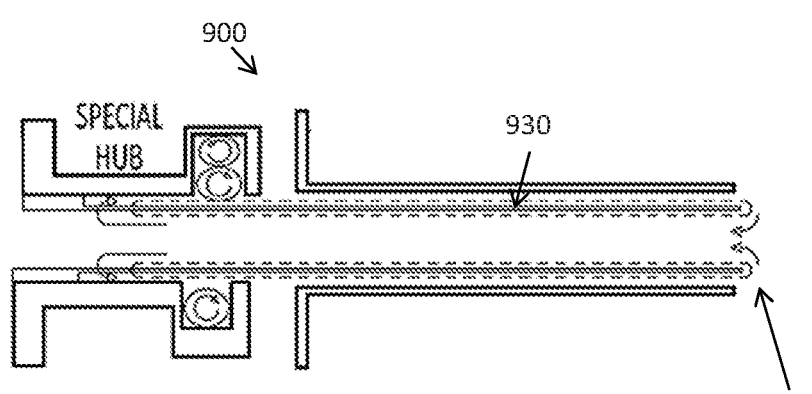
FIG. 9C illustrates a motorized or motor-driven (e.g., "power driven) continuous tractor that is loaded into a larger catheter (e.g., an intermediate catheter).

As mentioned above, any of the apparatuses described herein may be used with an additional outer catheter, including the powered apparatuses described herein. For example, FIG. 9C illustrates an example of a powered apparatus 900 used with an intermediate catheter having a larger OD than the powered mechanical thrombectomy apparatus. In this example, the length of the apparatus is slightly greater or almost equal to the length of the intermediate catheter 930, so that just the distal end region of the apparatus, including the inverting tractor (belts) is accessible and/or sticks out 933 of the intermediate catheter. Alternatively, the apparatus may be retracted into the outer (intermediate) catheter slightly, or may extend substantially from the end of the outer catheter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of removing a clot from a vessel using a mechanical thrombectomy apparatus including a catheter extending from a proximal end to a distal end, a puller extending distally within the catheter and a flexible and tubular tractor, wherein the tractor is coupled to a distal end region of the puller and further wherein the tractor is inverted over a distal end opening of the catheter so that the tractor extends proximally over the catheter, the method comprising:
   (a) advancing the puller distally within the catheter and within the vessel towards a clot, so that the tractor extends distally beyond the distal end opening of the catheter, forming a gap between the tractor and the distal end opening of the catheter;
   (b) advancing the catheter distally over the puller and into the gap;
   (c) repeating (a) and (b) until the distal end opening of the catheter is adjacent to the clot; and
   (d) drawing the clot into the catheter with the tractor by pulling the tractor proximally within the catheter so that the tractor rolls and inverts over the distal end opening of the catheter.

2. The method of claim 1, further comprising, while repeating (a) and (b), pulling the puller proximally within the catheter to invert a portion of the tractor over the distal end opening of the catheter.

3. The method of claim 1, wherein drawing the clot into the catheter further comprises advancing the catheter distally while pulling the puller proximally.

4. The method of claim 1, wherein advancing the puller distally comprises advancing the puller without using a guidewire extending distal to the puller.

5. The method of claim 1, wherein advancing the puller comprises extending the distal end of the puller out of the distal end opening of the catheter.

6. The method of claim 1, wherein advancing the puller comprises extending the tractor distally within the vessel, further wherein the tractor comprises a woven flexible and tubular tractor.

7. The method of claim 1, wherein advancing the puller comprises extending the tractor distally within the vessel, further wherein the tractor comprises a knitted tractor.

8. The method of claim 1, wherein advancing the puller comprises extending the tractor distally within the vessel, further wherein the puller comprises a central lumen configured to pass a guidewire therethrough.

9. The method of claim 1, wherein advancing the puller comprises advancing the puller within an internal carotid artery.

10. A method of removing a clot from a vessel using a mechanical thrombectomy apparatus including a catheter extending from a proximal end to a distal end, a puller extending distally within the catheter and a flexible and tubular tractor, wherein the tractor is coupled to a distal end region of the puller and further wherein the tractor is inverted over a distal end opening of the catheter so that the tractor extends proximally over the catheter, the method comprising:
   (a) advancing the puller distally towards the clot, so that the distal end region of the puller and the tractor extend distally beyond the distal end opening of the catheter;
   (b) advancing the catheter distally over the puller so that the distal end region of the puller is within the catheter;
   (c) repeating and alternating (a) and (b) until the distal end opening of the catheter is adjacent to the clot; and
   drawing the clot into the catheter with the tractor by pulling the tractor proximally within the catheter so that the tractor rolls and inverts over the distal end opening of the catheter.

* * * * *